United States Patent
Li

Patent Number: 5,376,376
Date of Patent: Dec. 27, 1994

[54] RESORBABLE VASCULAR WOUND DRESSINGS

[76] Inventor: Shu-Tung Li, 1 Kiowa Ter., Oakland, N.J. 07436

[21] Appl. No.: 46,895

[22] Filed: Apr. 15, 1993

Related U.S. Application Data

[63] Continuation of Ser. No. 821,384, Jan. 13, 1992, abandoned.

[51] Int. Cl.$^5$ .............................................. A61F 13/00
[52] U.S. Cl. .................... 424/443; 424/445; 606/108; 606/153; 606/154; 623/1; 623/12
[58] Field of Search .............. 424/443, 445; 606/108, 606/153, 154; 623/1, 12

[56] References Cited

U.S. PATENT DOCUMENTS

| | | | |
|---|---|---|---|
| 4,233,360 | 11/1980 | Luck | 424/443 |
| 4,503,569 | 3/1985 | Dotter | 623/1 |
| 4,740,207 | 4/1988 | Kreamer | 623/1 |
| 4,776,337 | 10/1988 | Palmaz | 606/108 |
| 5,024,841 | 6/1991 | Chu | 424/484 |
| 5,026,381 | 6/1991 | Li | 606/152 |
| 5,035,893 | 7/1991 | Shioya | 424/445 |
| 5,100,429 | 3/1992 | Sinofsky | 606/195 |
| 5,116,824 | 5/1992 | Miyata | 424/445 |

*Primary Examiner*—D. Gabrielle Phelan

[57] ABSTRACT

The present invention is related to prostheses, their methods of manufacture and methods for repairing vascular lesions using such prostheses. Natural polymers such as collagen are processed and fabricated to form tubular resorbable vascular wound dressings with unique physico-chemical and mechanical properties for repairing selected vascular segments, and for delivering therapeutic agents at selected sites within vessels and at the anastomoses.

14 Claims, 2 Drawing Sheets

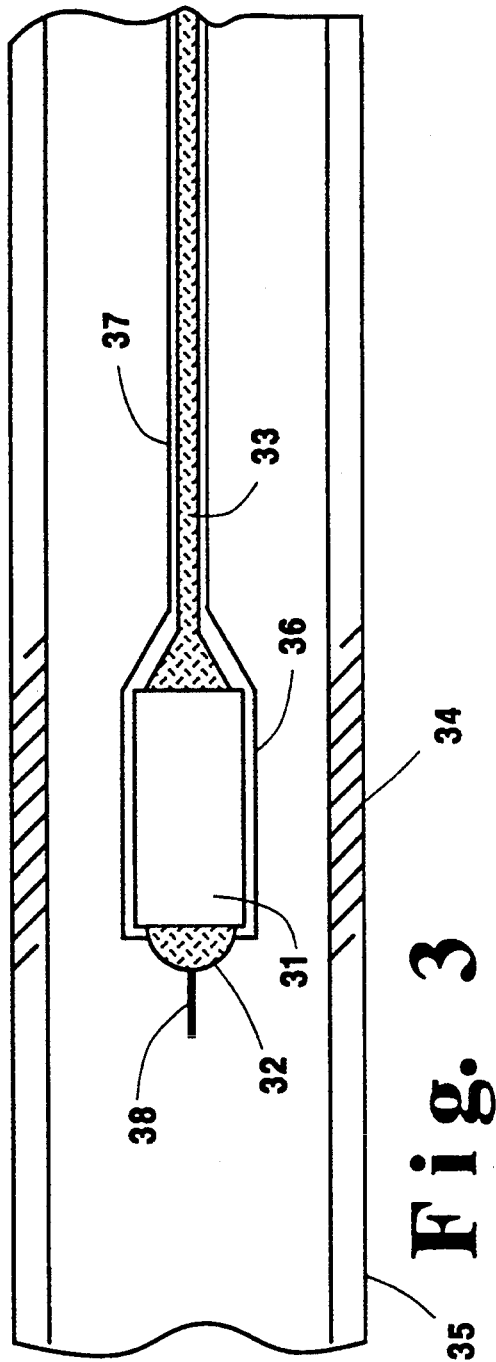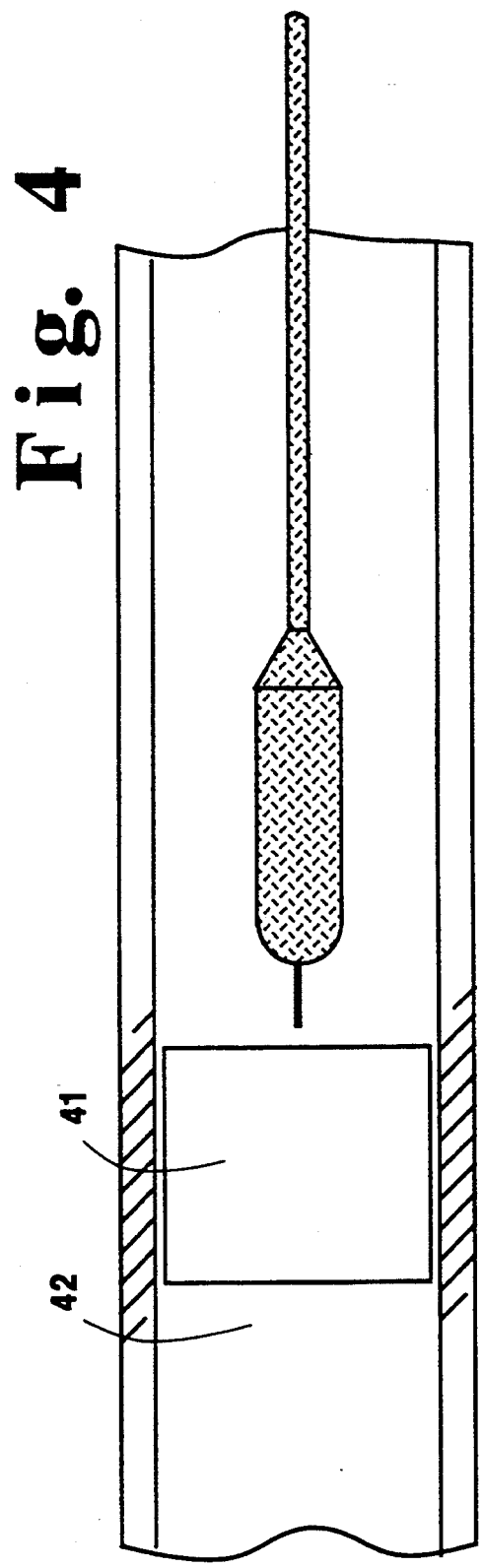

RESORBABLE VASCULAR WOUND DRESSINGS

This application is a continuation of prior U.S. application Ser. No. 07/821,384, filed Jan. 13, 1992, now abandoned.

FIELD OF INVENTION

This invention pertains to the field of interventional therapeutic approaches and surgical approaches to blood vessel repair and regeneration. More specifically, the present invention relates to the bioresorbable, biocompatible, non-thrombogenic, porous tubular vascular wound dressings comprised of collagen based material, which vascular wound dressings are used to repair damaged or diseased blood vessel segments so as to provide a segment of tubular vascular wound dressing to mechanically support the damaged or diseased vessel, to facilitate the regeneration of the host vessel, and to provide a means to deliver therapeutic agents at the selected sites. Methods of manufacturing the resorbable vascular wound dressings and methods of using the resorbable vascular wound dressings are disclosed.

BACKGROUND OF THE INVENTION

Prior to 1980, the most effective means of repairing diseased blood vessels was by surgery. A comprehensive review of the prior art of vascular surgery can be found in "Vascular Surgery" edited by Wesley S. Moore, Grune & Stratton, Inc. 1983. In one of the disclosed surgical procedures, a vascular graft (either biological or synthetic) is used to bypass the lesion to allow blood flow from the proximal to the distal end. Typically, in coronary artery repair procedures, an autogenous saphenous vein graft is used as a bypass graft to restore the normal blood flow in the heart. As surgical procedures of this kind are generally traumatic, requiring weeks of hospitalization and extensive surgical costs, alternative treatment methods have been sought. Percutaneous transluminal angioplasty (PTA) has since emerged to be the most popular method as the least traumatic interventional therapeutic approach for repairing atherosclerotic coronary and peripheral artery diseases in the past decade. There were approximately 300,000 angioplasty procedures for coronary artery diseases in the U.S. alone for 1988 (BBI Newsletter vol 13, No. 5, Table 4, Page 86, 1989). Despite the growth and acceptance of angioplasty, its overall success has been limited by vessel reclosures (abrupt reclosure and restenosis). Overall, vessel reclosure occurred in one third of cases over the past ten years. With the anticipated increase in angioplasty procedures in the coming years, a correspondingly greater number of patients will be affected as a result of vessel reclosure. The impact of vessel reclosure is therefore of major importance in terms of patient morbidity, repeat procedure risk, and increased health costs. It has been estimated that a reduction in the restenosis rate of 33% to 25% could save $300 million in overall healthcare costs. As such, an effective, reliable and safe method of reducing and perhaps preventing vessel reclosure is most welcome.

Many different approaches have been taken in an attempt to prevent post-angioplasty vessel reclosure. One such approach has been the use of an intravascular stent to mechanically keep the lumen open. One such stent is disclosed in U.S. Pat. No. 4,733,665, where an intravascular stent comprising of an expandable stainless steel wire mesh tube is used to prevent post angioplasty restenosis and vessel reclosure. The stent is positioned over an inflatable balloon secured to a catheter and is advanced to the stenosed region. The balloon is inflated, thereby expanding the stent into contact with the vessel wall. The elastic limit of the wire mesh is exceeded when the balloon is expanded, so that the stent retains its expanded configuration. U.S. Pat. No. 4,503,569 discloses a shape memory alloy stent which is advanced to a stenosed region on a catheter. The stent has the form of a coil spring. After the stent is in place, the stent is heated with a hot fluid causing the shape memory alloy to expand into contact with the blood vessel. Stents for blood vessel repair are also disclosed in U.S. Pat. Nos. 4,553,545 and 4,732,152. A plastic graft for repair of vascular system is disclosed in U.S. Pat. No. 4,740,207. U.S. Pat. No. 4,577,631 discloses a Dacron graft that is coated with an adhesive which may be activated by ultraviolet or ultrasonic energy after placement in the aorta. As most of these stents and grafts have been developed based on mechanical requirements, and are fabricated from metals, alloys, or plastics and remain in the blood vessel indefinitely, they generally have many disadvantages and limitations in fulfilling the requirements of an acceptable intravascular prosthesis which is in constant contact with the blood and is subjected to continuous pulsatile pressure in the body. The disadvantages of the prior art intravascular stents and grafts are discussed below.

Firstly, the selection of a blood compatible material is most critical in applications in contact with blood. Metals have high surface energy and are not blood compatible which may therefore induce acute thrombosis when implanted as an intraluminal or intravascular stent or graft. In addition, metals are non-resorbable and are subject to corrosion. Even the best stainless steel cannot be guaranteed that they will not corrode under the long term implantation conditions.

Secondly, compliance mismatch resulting in intimal hyperplasia and graft reclosure has been documented in many vascular grafting procedures. Metals are known to be non-compliant and it is not surprising that some chronic reclosure of the metal stent may be attributed to intimal hyperplasia formation. In fact, anastomotic hyperplasia as a result of compliance mismatch is still one of the major hurdles in developing a small diameter vessel for coronary bypass surgeries.

Furthermore, complete circumferential contact with the vessel endoluminal surface is critical for stent safety and efficacy. Incomplete expansion of the metal stent may be fatal. The continuous insult to the surrounding tissue due to pulsatile actions of the vessels may induce long term untoward effects. Moreover, metal stents have a fixed range of expansion within a blood vessel. In some cases the stent may be too small in diameter, even after expansion, to be affixed to the vessel wall, and in other cases, the stent may expand to such a diameter that the vessel is damaged or ruptured. In either case, improperly sized or positioned prior art stents require surgery for removal. The heat expandable metal, nitinol, has the additional disadvantage of incomplete expansion as a result of inadequate thermal exposure during deployment or from variabilities in stent material. Still further, migration of stents has been observed with prior art stents. Stent migration may be fatal. Stent migration may be due to under expansion, gradual change in metal properties, and the body's own defense to foreign material.

To circumvent some of the disadvantages of metal stents, Slepian, M. J. and Schindler, A. (Circulation, 78, Suppl IV: II-409, 1988) selected a synthetic polymeric material, linear aliphatic polyester for stent fabrication. This material is slowly degradable and has certain thermal properties that may be used to seal and pave the lumenal sites in situ. The investigators used a dual balloon deployment approach and melted the polymer in situ at 60° C. followed by balloon compression directed flow of the melt polymer for vessel sealing and subsequently cooling the material to solidify the polymer seal or pave. This approach has been referred to as polymeric endoluminal paving and sealing (PEPS) in the prior art. This PEPS approach may have several potential disadvantages. The high temperature may have an unknown effect on the local tissue and cells. The melting and recrystallization within a vessel may not be a predictable event in such a life-sustaining process. Further, the long term effects of the degraded products are unknown. The adhesion of the polymer film with the tissue also increases the risk of fragmentation of the material which may cause potential embolization.

There are many advantages of using type I collagen material for intravascular stent or wound healing applications which can not be simulated by metals and synthetic polymers. Type I collagen molecule is a triple helix and has a unique protein configuration that is a coiled coil of three polypeptide chains or alpha chains. Two of the alpha chains are identical and are called alpha 1 chains and the third chain is slightly different in amino acid composition and is called alpha 2 chain. Each alpha chain twists in a left-handed helix with three residues per turn, and three chains are wound together in a right-handed superhelix to form a rod-like molecule about 1.4 nanometer in diameter and 300 nanometer long. The alpha chains each contain about 1,050 amino acid residues and the molecular weight of a type I collagen molecule is about 300,000 daltons. In each alpha chain within the triple helix every third amino acid residue is a glycine. Collagen is characterized by a high content of proline and hydroxyproline residues, the absence of tryptophane, a minor amount of aromatic amino acid, and a significant amount of dicarboxylic and dibasic amino residues. At both ends of the collagen molecule three are terminal peptide sequences known as telopeptides which are globular and are not triple helical in structure and which lack glycine at every third residue. These telopeptides are the primary sites of intermolecular crosslinking in the molecule. Some of the advantages of using type I collagen for the applications of the present invention are briefly summarized below.

Firstly, type I collagen is hypo-immunogenic. Antibodies against type I collagen molecule of one species cannot be raised in the second species without the use of Freund's Complete Adjuvant. The immunogenicity is reduced when collagen is in the fiber form. Chemical crosslinking further reduces the immunogenicity to a non-detectable level. In other words, purified type I collagen fibers are highly biocompatible.

Secondly, type I collagen is biodegradable and the rate of biodegradation can be controlled by chemical means such as by crosslinking with glutaraldehyde, formaldehyde or other bifunctional crosslinking agents. There are a number of cells (macrophages, polymorphonuclear leukocytes and fibroblasts) that, during wound healing, secrete the enzyme collagenases which cleave collagen at $\frac{1}{4}$ position from the C-terminal end of the molecule. The two short triple-helices are not stable at body temperature and are denatured to random coiled peptides which are then degraded into amino acids and small peptides by proteases in the body. The amino acids and peptides are metabolized, presumably through the normal pathways similar to the resorption of host collagen during remodeling of the wound.

Further, type I collagen molecule has about 250 amino and guanidino groups (positively charged groups at pH 7.4) and about 250 carboxyl groups (negatively charged groups at pH 7.4). These side chain functional groups are reactive and can be modified by chemical means to change its physico-chemical, mechanical and biological properties. For example, native type I collagen fibers are thrombogenic. However, the thrombogenicity of the collagen can be significantly reduced when the collagen molecule is modified to a negatively charged protein.

Still further, type I collagen can be prepared either as a solution or as a highly swollen fibrillar dispersion such that medicaments in the form of small molecular drugs, peptides and macromolecules can be incorporated into the collagen fibers to form a composite material that would function as a vehicle for slow systemic release or as a local delivery system of the medicaments.

Repair of other tissues such as skin, nerve and meniscus cartilage has been attempted using type I collagen containing material. For example, Yannas et. al. fabricated an endodermal implant using collagen-glycosaminoglycan composite material (U.S. Pat. No. 4,060,081). Li used a semipermeable, resorbable type I collagen conduit for peripheral nerve repair (U.S. Pat. No. 4,963,146). Stone used biocompatible, resorbable type I collagen-glycosaminoglycan matrices to regenerate meniscus cartilage (U.S. Pat. No. 5,007,934).

A collagen wound healing matrix is disclosed in U.S. Pat. No. 5,024,841. This wound healing matrix is made from atelocollagen (pepsin solubilized skin collagen) and is not chemically crosslinked. As such, it does not possess the unique physico-chemical and mechanical properties that are critically required for the specific vascular applications of the present invention.

However, even with the various foregoing technologies which have been applied to repair damaged or diseased anatomical structures, a device successful as a vascular wound dressing and constructed from totally resorbable natural materials, or analogs thereof, has not been developed in the prior art.

Accordingly, it is an object of the present invention to provide improved vascular wound healing devices, which provide structural support to the damaged or diseased vessel segment, allowing normal blood flow.

It is another object of the present invention to provide vascular wound dressings which are biocompatible, bioresorbable, hemocompatible, and compliant.

It is a further object of the present invention to provide vascular wound dressing devices which when released at the selective sites inside a blood vessel will self expand to adhere to the vessel wall via hydration of the material.

It is a yet another object of the present invention to provide a means to deliver medicaments to the selective sites either intravascularly or extravascularly for therapeutic applications.

It is still another object of the present invention to provide a means to manufacture the vascular wound dressings.

It is yet a further object of the present invention to provide a means to repair the damaged or diseased blood vessel.

SUMMARY OF THE INVENTION

By means of the present invention, resorbable vascular wound dressings for blood vessel repair have been discovered which eliminate or substantially reduce many of the disadvantages and problems associated with the prior attempts at vessel repair in angioplasty procedures. In addition, by means of the present invention, a method is provided to deliver medicaments to the selected sites inside or outside a blood vessel. More specifically, by means of the present invention, resorbable wound dressings have been discovered which prevent or substantially reduce the risk of post-angioplasty vessel reclosure, which vascular wound dressings are tubular, compliant, self-expandable, low-profile, biocompatible, hemocompatible and bioresorbable.

The resorbable vascular wound dressings of the present invention are generally dry, porous matrices of type I collagen containing fibers in a cylindrical form with varying inside and outside diameters. In a preferred form of the invention, the fibers are randomly oriented throughout the matrix to provide radial compliance to the wound dressings.

The matrices may also include selected medicaments for local therapeutic applications. Therapeutic medicaments include anti-platelet agents such as aspirin and the like, anti-coagulant agents such as coumadin and the like, antibiotics, anti-thrombus deposition agents such as polyanionic polysaccharides including heparin, chondroitin sulfates, hyaluronic acid and the like, urokinase, streptokinase, plasminogin activators and the like, wound healing agents such as transforming growth factor beta (TGF beta) and the like, glycoproteins such as laminin, fibronectin and the like, various types of collagens.

In particular, the self-expandable vascular wound dressing of the present invention comprises a conduit having walls comprised of type I collagen matrix material having pores with an average diameter of from about 0.1 um to about 150 um and an inwardly converging tapered inner diameter.

Further, the invention includes a method for fabricating resorbable vascular wound dressings.

This method comprises:
a) forming an aqueous dispersion containing type I collagen;
b) coacervating the collagen with a coacervating agent;
c) placing the coacervated collagen fibers into a coaxial cylindrical mold;
d) freeze drying the fibers in the mold to form a dried collagen matrix conduit;
e) spraying the freeze dried collagen matrix conduit with water mist;
f) compressing the water mist treated collagen matrix conduit;
g) compressing the ends of the collagen matrix conduit to form an inwardly convergining tapered inner diameter; and then
h) crosslinking the compressed collagen matrix conduit with a crosslinking agent.

Still further, the invention includes a method for treating a damaged or diseased blood vessel with resorbable vascular wound dressings. The method includes delivering the resorbable vascular wound dressing in a folded configuration to the selected site via a conventional catheter and releasing the resorbable vascular wound dressing at the selected site where the wound dressing self expands to its original configuration and adhere to the vessel wall. In particular, this method comprises:
a) inserting a delivery catheter containing the wound dressing through a percutaneous site into an artery;
b) guiding the wound dressing to the selective intravascular site with a guide wire; and then
c) releasing the vascular dressing at the intravascular site.

Moreover, the invention includes a method for delivering resorbable vascular wound dressings at the anastomotic sites inside or outside a blood vessel during vascular surgery. In particular, the method for delivering a vascular wound dressing at the anastomotic site inside a blood vessel comprises:
a) inserting a vascular wound dressing into the lumens of a host vessel and a vascular graft at the anastomotic sites; and then
b) aligning the host vessel and the vascular graft and suturing the graft to the host vessel at both the proximal and distal ends of the graft.

Further, the method for delivering a vascular wound dressing at the anastomotic site outside a blood vessel comprises:
a) inserting the host vessel or the vascular graft into the vascular wound dressing;
b) performing anastomosis of the host vessel and vascular graft;
c) pulling the wound dressing to cover the anastomotic sites at both the proximal and distal ends.

Particularly, the resorbable vascular wound dressings of the present invention are constructed such that the walls are substantially porous to permit nutrient diffusion for promoting endothelialization, facilitating tissue ingrowth and hastening anchorage with the host vessel. Further, the lumenal surface is non-thrombogenic and effectively prevents thrombus deposition. Still further, the resorbable wound dressings have a compliance similar to the host vessel for compliance match, reducing the potential risk of intimal hyperplasia formation. Moreover, the resorbable wound dressings have low profile walls which further reduce flow disturbances at the dressing vessel junctions. The porous walls of the resorbable vascular wound dressings provide an initial scaffold for host vessel regeneration.

Thus, in a preferred embodiment of the present invention, the resorbable vascular wound dressings of the present invention have the following physical characteristics and physico-chemical properties:

| Physical Characteristics: | |
| --- | --- |
| Inside Diameter (mm) | 2–30 |
| Pore size (um) | 0.1–150 |
| Wall Thickness (mm) | |
| Distal Ends | 0.05–0.30 |
| Center | 0.10–1.5 |
| Density (g/cm$^3$) | 0.05–0.80 |
| Length (cm) | 0.5–15 |

| Physico-chemical Properties: | |
| --- | --- |
| Compliance (% radial change/mm Hg $\times 10^2$) | 2.0–7.0 |
| Swelling Capacity (g/g) | 0.5–15 |
| Thermal Stability (°C.) | 55–85 |

| -continued | |
|---|---|
| Physico-chemical Properties: | |
| Relaxation Recovery Time (second) | 1–30 |

The invention will next be described in connection with certain illustrated embodiments.

BRIEF DESCRIPTION OF THE DRAWINGS

The foregoing and other objects of this invention, the various features thereof, as well as the invention itself, may be more fully understood from the following description, when read together with the illustrated embodiments.

FIG. 3. shows a cross-sectional view of a delivery catheter having a resorbable vascular wound dressing folded over a balloon inside a protective sheath within a blood vessel in accordance with the present invention.

FIG. 4 shows a cross-sectional view of a deployed resorbable vascular wound dressing inside a blood vessel.

DESCRIPTION OF THE INVENTION

It has been discovered that the resorbable vascular wound dressings having specific characteristics can be fabricated from type I collagen containing material and can be introduced to the lesion site either intraluminally via a catheter or at the anastomatic sites during surgery, which wound dressings will eliminate or substantially reduce many of the disadvantages of the prior art metal and synthetic polymeric devices for vascular repair. Each unique characteristic and property of the resorbable vascular wound dressings and their advantages over the prior art are summarized below.

Firstly, the resorbable vascular wound dressings of the present invention have walls comprised of type I collagen material which is biocompatible and is further chemically modified for blood contact applications.

Secondly, walls of the resorbable vascular wound dressings of the present invention are porous having pores from about 0.1 um to about 150 um that are tortuously arranged to facilitate anchorage of the walls with the host tissue via cellular infiltration. The porous nature of the wound dressing also allows nutrient diffusion through the walls, thus facilitating endothelialization.

Figure 1:
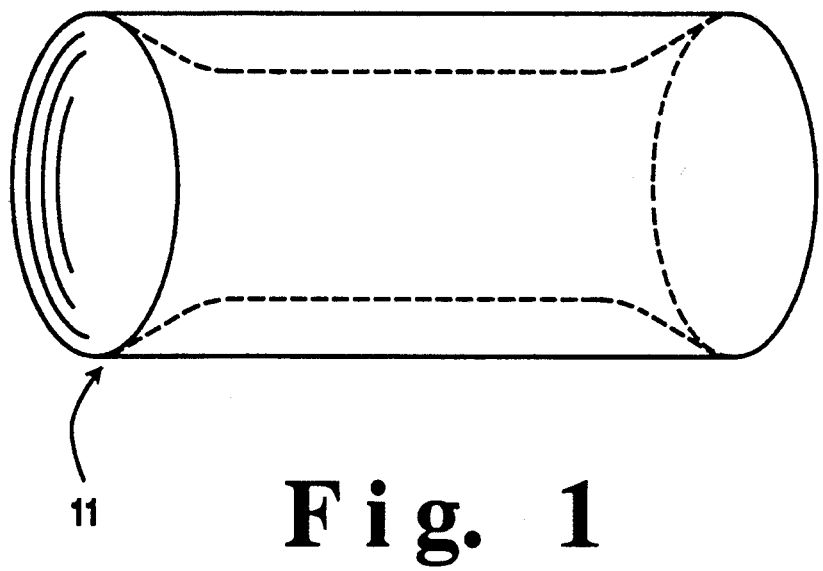
FIG. 1 shows a perspective view of a resorbable vascular wound dressing made in accordance with the present invention.
Figure 2:
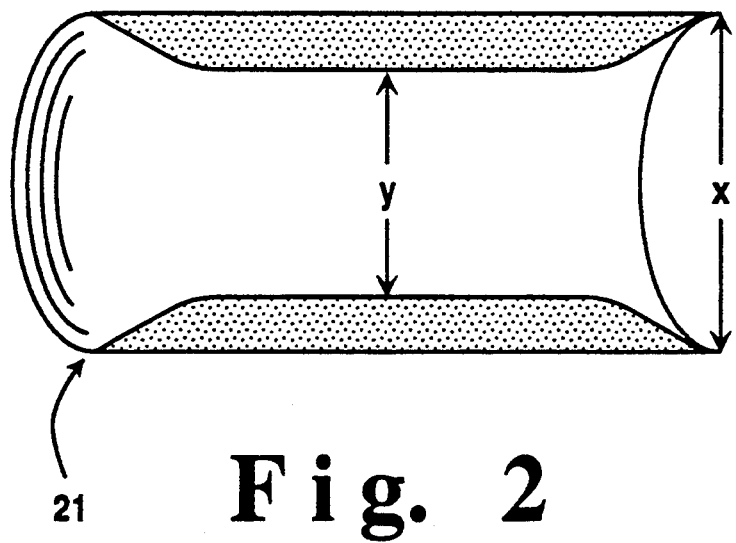
FIG. 2 shows a longitudinal cross-sectional view of the resorbable vascular wound dressing.

Further, the resorbable vascular wound dressings of the present invention have low profile walls at the distal ends as shown in member 11 of FIG. 1 and member 21 of FIG. 2. The walls are tapered such that the inner diameter X at the ends of the dressing are greater than the inner diameter Y at the center portions of the dressing. By means of this construction, the blood flows with minimal disturbance, thus reducing the risk of blood stasis and eddy current which may damage the blood cells and cause subsequent accumulation of thrombus. In particular, the walls of the present invention have a thickness from about 0.1 mm to about 1.5 mm in the center part of the wound dressing and from about 0.05 mm to about 0.3 mm at the ends of the wound dressing.

The density of the resorbable vascular wound dressings of the present invention may vary from about 0.05 g/cm$^3$ to about 0.8 g/cm$^3$, where "g/cm$^3$" is a unit connoting the number of grams of wound dressing in a cubic centimeter of matrix, to accommodate various mechanical and therapeutic requirements of the wound dressings. For example, a lower density wound dressing may be more advantageous in applications where a rapid diffusion of therapeutic agents is required.

The resorbable vascular wound dressings of the present invention have a compliance which is in the range of normal blood vessels. Compliance match between the host vessel and the implant is important. Compliance mismatch at the host vessel-implant junctions may result in turbulent blood flow and thrombus deposition, leading to smooth muscle cell proliferation and eventual occlusion. The resorbable vascular wound dressings of the present invention have a compliance from about 2.0% radial change per mm Hg$\times 10^{-2}$ to about 7.0% radial change per mm Hg$\times 10^{-2}$, preferably from about 4.0% radial change per mm Hg$\times 10^{-2}$ to about 6.0% radial change per mm Hg$\times 10^{-2}$. The resorbable vascular wound dressings of the present invention are hydrophilic which facilitates cell infiltration for rapid anchorage to the host vessel wall. The swelling capacity of the resorbable vascular wound dressings may vary from about 0.5 g/g wound dressing to about 15 g/g wound dressing, preferably from about 2 g/g wound dressing to about 10 g/g wound dressing.

The rate of resorption of the resorbable vascular wound dressings of the present invention may be advantageously designed for a specific lesion site application. For example, slower in vivo resorption may be more advantageous in applications where mechanical support function of the device is critical. The rate of in vivo resorption can be controlled by chemical means such as by using bifunctional intermolecular crosslinking agents such as glutaraldehyde, formaldehyde or the like. The in vivo rate of resorption is correlated with thermal shrinkage temperature of the material. The thermal shrinkage temperature of the resorbable wound dressings of the present invention is from about 55° C. to about 85° C., preferably from about 60° C. to about 75° C. The vascular wound dressings having a shrinkage temperature of from about 55° C. to about 85° C. is resorbable in vivo in about 30 days to about 120 days.

Referring now to FIGS. 3 and 4, the resorbable vascular wound dressing 31 of the present invention can be folded over the balloon 32 at the tip of a catheter 33, to facilitate delivery via a guide wire 38 to the specific lesion site 34 within a blood vessel 35. Upon release of the device via a pull of the string 37 to remove the protective sheath 36, the wound dressing unfolds and self expands to its full original geometry 41 when in contact with blood 42 within a blood vessel. This self expandability of the wound dressings is of particular importance in using the wound dressings for intravascular applications. The relaxation recovery time, which is defined as the time required for the wound dressing to transform from the folded geometry to the expanded geometry, is short for the wound dressings of the present invention. The relaxation recovery time of the resorbable wound dressings of the present invention is from about 1 second to about 30 seconds, preferably from about 3 seconds to about 10 seconds. Generally, in preparing the resorbable vascular wound dressings of the present invention, a collagenous tissue is first subjected to purification and chemical modification procedures.

In particular, the collagen material of the present invention may be prepared by the following methods.

First, a native source of type I collagen, such as skin, tendon, ligament, or bone is first cleaned of fat, fascia and other extraneous matter and washed. The cleaned and washed collagen containing material is then comminuted by slicing or grinding followed by extensive washing in water to remove soluble blood proteins.

The comminuted material is then subjected to a defatting treatment using fat solubilizing agents such as low molecular weight alcohols, including ethanol and propanols, ethers, such as ethyl ether, petroleum ether, or a mixture of ether and alcohol at approximately equal volumes. The defatted material is washed to remove the residual alcohol and/or ether.

The defatted and washed collagen containing material is then extracted with a neutral salt solution at a concentration of about 1M and a temperature of from about 4° C. to about 25° C. by means well known in the art. Neutral salt solution of high ionic strength weakens the electrostatic interactions between the collagen and non-collagenous materials. Such neutral salts include sodium chloride, potassium chloride and the like. By doing so, the neutral salt soluble non-collagenous materials are removed. The collagen material is then washed with deionized, distilled water.

The salt extracted collagen containing material is further purified by a process which subjects the collagen containing material to two extreme pH extractions in the presence of a structure stabilizing salt. The swelling at pH from about 2 to about 3 is accomplished by means well known in the art, such as with a suitable acid. Such acids include hydrochloric acid, acetic acid, lactic acid, or the like. The salt used may be sodium chloride, ammonium sulfate, sodium sulfate, or the like. Preferably, the acid extraction is performed at 4° C. to minimize the bacteria growth. The acid weakens the ionic interactions between collagen and acidic non-collagenous proteins which are solubilized and removed. After extensive washing with deionized, distilled water, the collagen is extracted with a basic solution at a pH above 13 by means well known in the art. Such bases include sodium hydroxide, potassium hydroxide, calcium hydroxide, and the like. The alkaline condition weakens the ionic interactions between collagen and basic non-collagenous materials which are solubilized and removed. The alkaline treatment also reduces the isoionic point due to partial deamidation of the glutamine and asparagine residues of collagen. The alkaline extracted collagen material is then extensively washed with deionized, distilled water to remove the residual base and to lower the pH to from about 5 to about 7.

The base extracted collagen is then chemically modified to partially acetylate the epsilon-amino groups of collagen to remove the positively charged epsilon-amino groups so as to further lower the isoionic point for hemocompatibility. Methods for acetylating the epsilon-amino groups of collagen are well known in the art such as by reacting with acetic anhydride in the presence of half saturated sodium acetate at a pH of about 8.0. Alternatively, the hemocompatibility may be enhanced by increasing the total number of negatively charged groups by subjecting the collagen to succinylation with succinic anhydride at a pH of about 8.0. By doing so, additional negative charged carboxyl groups are attached to the side chains of lysine residues.

The thusly prepared type I collagen material maintains fibrillar structure, contains minimal non-collagenous impurities and is well suited for additional processing for the preparation of the resorbable vascular wound dressings of the present invention. However, it must be appreciated that other types of collagen such as type II collagen, type III collagen and the like from the natural tissues may also be prepared for the intended use of the present invention.

In preparing a resorbable vascular wound dressing of the present invention, the purified and chemically modified collagen is first used for the preparation of a dispersion in a manner well known in the art. One such preparation of collagen dispersion is taught in U.S. Pat. No. 3,157,524 which is incorporated herein by reference as if set out in full. In particular, the collagen dispersion of the present invention may be prepared by the following method.

The purified type I collagen is first swollen with an acid solution such as hydrochloric acid, phosphoric acid, lactic acid, acetic acid and the like. Regardless of which acid is used, the pH of the acid collagen dispersion is in the range of from about 2 to about 3.

The swollen collagen is then homogenized by any conventional means such as a homogenizer or blender so as to further dissociate the fibers. The homogenized collagen dispersion is then filtered to remove unswollen aggregates by means well known in the art such as by filtering through a stainless steel mesh or the like under vacuum.

In one embodiment of the present invention, if the resorbable vascular wound dressing is further intended to function as a medicinal delivery vehicle, then in addition to the type I collagen, various medicaments may optionally be present in the dispersion such as aspirin, coumadin, antibiotics, polyanionic polysaccharides such as heparin, hyaluronic acid, chondroitin sulfates and the like, growth factors such as transforming growth factor beta (TGF beta) and the like, prostaglandins, plasminogen activators, urokinase, streptokinase, glycoproteins such as fibronectin, laminin and the like, type II through type XII collagens.

The resorbable vascular wound dressings may be formed from the collagen dispersion by the following embodiments depending on the size and mechanical requirements of the wound dressings.

In one preferred embodiment of the present invention, the collagen fibers in the dispersion is first coacervated by adjusting the pH to its isoionic point using a base well known in the art, such as with a sodium hydroxide, ammonium hydroxide or the like. The coacervated fibers are fully phase separated from the water and are removed using tongs into a perforated centrifuge tube. The excess water associated with the hydrated fibers is removed by centrifuge at a low velocity using a commercial centrifuge. The partially dehydrated fibers are then fitted into a cylindrical mold which mold contains a rod in the center of the cylinder. The diameter of the rod defines the diameter of the lumen of the resorbable vascular wound dressing. The molded collagen fibers are then subjected to a freeze drying procedure using a commercial freeze dryer, which procedure is well know in the art. Typically, the collagen fibers are first frozen at a temperature below −20° C. from about 4 hours to about 8 hours, followed by drying at −10° C. for about 24 hours to about 48 hours and then at 20° C. for about 4 hours to about 8 hours at a vacuum from about 50 um Hg to about 300 um Hg. The thusly formed tubular porous matrix is allowed to stand overnight at room temperature to relax the fibers due to excessive vacuum treatment. The collagen fibers in the matrix prepared this way are randomly oriented so as to provide mechanical strength and compliance in both the longitudinal and radial directions. This is of particular importance in small diameter (less than 6 mm) vessel repair applications where compliance match of the wound dressing to the host vessel must be considered for efficacy. The freeze dried matrix with the rod attached is then inserted into a stirrer which rotates the matrix at a velocity of from about 20 rpm to about 700 rpm, preferably from about 40 rpm to about 400 rpm. A stream of water mist is sprayed onto the surface of the matrix from a distance of from about 6 inches to about 18 inches for about 5 seconds to about 30 seconds while the matrix is being rotated. Any commercial water sprayer such as the Compressed Air Sprayer from Consolidated Plastics Company, Inc. may be used for this purpose. The spray of water mist facilitates the compression process similar to the garment and laundry industries which are common in every household practice.

The water mist treated tubular porous matrix is subjected to dual rotational compression in order to reduce the wall thickness. The first rotational compression step is carried out by means well known in the art such as by rotation while compressing against a smooth solid wall such as a glass surface or a plastic surface or by compressing the porous cylinder between two smooth solid surfaces during rotation. Preferably, the outside diameter of the compressed matrix may be defined by the predetermined gap distance of the two solid plates. Specifically, depending upon the internal diameter of the wound dressing, the thickness of the wall may be made according to the following formula:

Internal diameter of the wound dressing (I.D.) + 2 × wall thickness = outside diameter (O.D.)

or $$\text{Wall thickness} = \frac{O.D. - I.D.}{2}$$

Where O.D. equals the gap distance between the plates. Preferably, the wall thickness is from about 0.1 mm to about 1.5 mm.

The second compression step is carried out at the two ends of the tube to further reduce the profile of the wound dressing at the distal ends so as to form the desired taper. This is carried out by inserting a tapered plug (a frustum of a right circular cone) at each end of the tubular matrix. Depending upon the I.D. and O.D. of the tubular matrix, the upper base of the frustum of the right circular cone has a diameter equal to the I.D. of the tubular matrix and the other end, lower base of the frustum of the right circular cone, has a diameter which is about 0.1 mm to about 0.6 mm smaller than the O.D. such that the inside diameter at the distal ends of the final compressed vascular wound dressing has a wall thickness of from about 0.05 mm to about 0.3 mm.

Alternatively, the central rod of the mold may be cone shaped (a frustum of a right circular cone with the lower base pointing outward) at each end which dictates the size of the lumen and the wall thickness at the central portion and the ends of the resorbable vascular wound dressing upon completion of the compression step of the freeze dried matrix. The I.D. at the center and at the ends and the wall thickness of the resorbable vascular wound dressing may be defined by the diameter of the mandrel, the size of the upper base and the lower base of the frustum of the right circular cone and the gap distance between the two compressed plates.

The thusly compressed tubular matrix is then subjected to a crosslinking step by methods well known in the art, such as by contacting the matrix to a bi-functional crosslinking agent including formaldehyde, glutaraldehyde, carbodiimides and the like in the vapor phase or in the liquid phase. Crosslinking controls the in vivo stability of the vascular wound dressings and also fixes the geometrical configuration which provides the self expandability of the wound dressings when the dressings are mechanically deformed and in contact with an aqueous solution. Preferably, the crosslinking is performed in the vapor phase. Particularly, when crosslinking is performed in the vapor phase, the crosslinking may be achieved through vapors of formaldehyde, glutaraldehyde or the like at a relative humidity of from about 75% to about 100% and at a temperature of from about 20° C. to about 30° C.

Alternatively, the crosslinking may be achieved through an endothermic chemical condensation of the intermolecular side chains of collagen at a temperature between 95° C. to 110° C. and a vacuum between about 10 um Hg to about 100 um Hg for about 24 hours, known in the art as dehydrothermal crosslinking.

In another embodiment of the present invention where the radial mechanical strength of the resorbable vascular wound dressing is important, it may be desirable to have the mandrel wound with a resorbable filament such as a collagen filament or a polyglyconate, a polylactate, a polyglyconatepolylactate co-polymer filament or the like. The resorbable filament incorporates into the walls of wound dressings to provide additional rigidity to the vascular wound dressing for mechanical support requirement.

Alternatively, the rigidity of the wall may be further increased by aligning the fibers in the circumferential direction. This may be accomplished by first inserting the filament wound mandrel into a mechanical stirrer and rotating the mandrel at a speed from about 10 rpm to about 60 rpm so as to slowly wrap the partially dehydrated fibers onto the coiled filament. The filament impregnated fibers may be further dehydrated by slowly rotating against a smooth surface such as glass before feeze drying.

The extent of crosslinking of the vascular wound dressing can be measured by the hydrothermal shrinkage temperature of the wound dressing, i.e. the temperature at which the wound dressing in an aqueous environment begins to shrink due to unfolding of the collagen triple helix. The method for measuring the shrinkage temperature of a collagen material is well known in the art. Typically, a segment of a vascular wound dressing is first equilibrated in a 0.2M phosphate buffered solution bath at pH 7.4 at about 25° C. for about 10 minutes to about 30 minutes. The length of the wound dressing is determined by a cathetometer. The temperature of the solution is then raised by heating the solution at a rate of about 1° C. per minute. The length of the wound dressing is continuously recorded. The shrinkage temperature is defined as that temperature at which 50% reduction in the wound dressing length is reached. Alternatively, shrinkage temperature may be measured by a commercial apparatus such as a differential scanning calorimeter. Generally, the degree of crosslinking is such that the shrinkage temperature of the resorbable vascular wound dressing is in the range of from about 55° C. to about 85° C., preferably from about 60° C. to about 75° C. Such wound dressings are crosslinked to such an extent they are completely resorbed within 1 to 4 months when in the body.

By virtue of having made the resorbable vascular wound dressings in accordance with the above procedure, the dressing has a low profile wall at the distal and proximal ends to minimize the blood flow disturbance, a compliance match with the host vessel to minimize the hyperplasia, and a porous wall to facilitate cell infiltration whereby promoting adhesion of the wound dressing to the host vessel to prevent dressing migration. Further, such a wound dressing will facilitate wound healing and host vessel regeneration, permit nutrient exchange, and facilitate endothelialization. Moreover, such a wound dressing can be mechanically deformed and it subsequently returns to its original configuration when in contact with an aqueous solution. More specifically, in order to accomplish this desired selectivity, the vascular wound dressings have the following physical characteristics: wall thickness from about 0.1 mm to about 1.5 mm in the center of the wound dressing and from about 0.05 mm to about 0.3 mm at the ends of the wound dressing; inside diameter from about 2 mm to about 30 mm; length from about 0.5 cm to about 15 cm; pores in the range of from about 0.1 um to about 150 um; density from about 0.05 g/cm$^3$ to about 0.8 g/cm$^3$. Further, in order to accomplish this desired selectivity, the vascular wound dressings have the following physico-chemical properties: compliance from about 2.0% radial change per mm Hg$\times 10^{-2}$ to about 7.0% radial change per mm Hg$\times 10^{-2}$, preferably from about 4% radial change per mm Hg$\times 10^{-2}$ to about 6% radial change per mm Hg$\times 10^{-2}$; swelling capacity from about 0.5 g/g to about 15 g/g, preferably from about 2.0 g/g to about 10 g/g; thermal shrinkage temperature from about 55° C. to about 85° C., preferably from about 60° C. to about 75° C.; relaxation recovery time from about 1 second to about 30 seconds, preferably from about 3 seconds to about 10 seconds.

The resorbable vascular wound dressings made in accordance with the present invention possess unique properties not only to function as a intravascular stent to prevent or significantly reduce post-angioplasty vessel reclosure, but to repair vascular lesions resulting from annurysms and to deliver specific therapeutic agents to selective sites inside a blood vessel or at the anastomotic sites for therapeutic applications.

Specifically, in applications as a coronary artery wound dressing after angioplasty procedures, the low profile wall and the compliance of the intracoronary wound dressing of the present invention significantly reduce the risk of blood flow disturbance at the dressing-host vessel junction and minimize the risk of intimal hyperplasia. When in the presence of an anti-thrombogenic and an anti-smooth muscle cell proliferation agent such as heparin and the like, the slow release of the heparin and the like at the wound dressing surface further protects the surface from thrombus adhesion and intimal hyperplasia formation, while the dressing is slowly replaced by the regenerated host tissue.

In peripheral and aortic artery repair where the diameter of the vessel is in the range from about 6 mm to about 30 mm, mechanical support may be obtained by incorporating a resorbable supporting filament into the walls, such as collagen, polyglyconate, polylactate and the like.

In use, the resorbable vascular wound dressings of the present invention may be advantageously delivered to the selected site of an artery via a catheter to be used after the angioplasty procedure. Again referring to FIGS. 3 and 4, the vascular wound dressing is folded over the balloon at the tip of a percutaneous transluminal angioplasty (PTA) catheter covered with a tubular protective sheath which is attached to a string (FIG. 3). The sheath and the string may be made of any hemocompatible material including silicone and polyurethane. Upon positioning of the wound dressing at the lesion site via a guide wire and removing of the protective sheath via the pull of the string, the vascular wound dressing self expands as it rehydrates to conform to the walls of the treated vessel. The balloon may be inflated to bring the vascular wound dressing into its maximal expansion within the artery. The balloon is then deflated and the catheter is removed upon the completion of the procedure, leaving the expanded vascular wound dressing at the selected site as shown in FIG. 4.

In another use, the resorbable vascular wound dressing may be folded over the balloon and delivered to the lesion site during the angioplasty procedure. Upon the removal of the protective sheath via the pull of the string, the balloon is inflated to push the vascular wound dressing to its maximum dimension, thereby opening the vessel for normal blood flow. The balloon is deflated and the catheter is removed, leaving the wound dressing at the lesion site.

In a further use, the resorbable vascular wound dressings of the present invention may be advantageously used to deliver medicaments inside a blood vessel. The vascular wound dressing incorporated with the medicaments may be advanced to the selected site of a vessel. Upon the removal of the protective sheath via the pull of the string, the vascular wound dressing self expands to adhere to the host vessel wall, leaving the desired medicaments at the specific site. Furthermore, if so desired, a radiopaque material such as BaSO$_4$ may be incorporated into the vascular wound dressing for easy visualization.

In still another use, the resorbable vascular wound dressings of the present invention incorporated with medicaments may be advantageously delivered to the anastomotic sites either inside a vessel or outside a vessel during surgery to protect the anastomotic sites from hyperplasia formation.

While there have been shown and described what are at present considered the preferred embodiments of the present invention, it will be obvious to those skilled in the art that various changes and modifications may be made without departing from the spirit and scope of the invention as defined by the appended claims.

The above and other objectives, advantages and features of the present invention will be better understood from the following non-limiting descriptions of theoretical and actual examples of producing and using the vascular wound dressings of the present invention.

EXAMPLE 1

Preparation of the Purified, Chemically Modified Collagen Fibers

The fat and fascia of bovine flexor tendon are carefully removed and washed with water. The cleaned tendon is frozen and comminuted by slicing into 0.5 mm slices with a meat slicer. The tendon is first defatted with isopropanol (tendon:isopropanol=1:5 V:V) for 8 hours at 25° C. under constant agitation. The extractant is decanted and an equal volume of isopropanol is added and the tendon slices is extracted overnight at 25° C. under constant agitation. The defatted tendon is extensively washed with deionized, distilled water to remove the residual isopropanol. The tendon is then extracted with 10 volumes of 1M NaCl for 24 hours at 4° C. under agitation. The salt extracted tendon is washed with deionized, distilled water to remove the salt. The salt extracted collagen is then extracted in 10 volumes of 0.05M lactic acid solution, in the presence of 0.35M sodium sulfate at pH 2.5 for 24 hours at 4° C. under constant agitation. The partially swollen collagen is deswelled by slowly adding 1M NaOH to fully coacervate the collagen fibers. The coacervated fibers are collected with a stainless steel strainer. After washing with deionized, distilled water, the fibers are extracted with 10 volumes of 0.75M NaOH for 24 hours in the presence of 1M $Na_2SO_4$ at 25° C. under constant agitation. The alkaline extracted collagen is collected with a strainer, neutralized with 0.1M HCl and washed with deionized, distilled water.

The thusly purified collagen is then chemically modified with acetic anhydride in the presence of half saturated sodium acetate at room temperature. Acetic anhydride is slowly added through a burette to the sodium acetate solution while the pH of the solution is continuously monitored and adjusted with 1M NaOH solution to 8. The reaction is continued for 2 hours. The partially acetylated collagen is then washed with deionized, distilled water, freeze dried and stored dry until use.

EXAMPLE 2

Preparation of Resorbable vascular wound Dressings

An aliquot of the purified fibers prepared in Example 1 is suspended in 0.05M lactic acid solution. The amount of fibers and acid solution used is such that a 1.0% (w/v) of collagen suspension is formed. The swollen fibers are then homogenized in a stainless steel blender for 60 seconds. The dispersed collagen fiber material is filtered through a 40 um stainless steel mesh with vacuum using a filter flask.

5 grams of homogenized, filtered collagen dispersion is weighed into a beaker. 0.3% $NH_4OH$ is slowly added to coacervate the fibers. The coacervated fiber is first dehydrated to the extent that it will fit into a coaxial cylindrical mold of 1.2 cm diameter, 2 cm long and a 0.4 cm rod in the center of the mold.

The collagen containing mold is then subjected to a freeze drying procedure using a Virtis commercial freeze dryer. The freeze dried tubular collagen sponge matrix is equilibrated at room temperature overnight. The mandrel with the collagen matrix is then fit into a stirrer. A stream of water mist is sprayed onto the collagen matrix from a distance of 12 inches while the rod is spinning at 200 rpm. The water mist treated collagen matrix is allow to stand for 10 minutes and the collagen matrix is then subjected to a rotational compression procedure using two plates with a gap distance of 0.46 cm. The compressed tubular collagen matrix is then subjected to a second compression procedure by inserting frustums of a right circular cone at the ends of the tubular matrix to reduce the wall thickness at the ends to about 0.1 mm. The compressed tubular collagen matrix is then crosslinked in a formaldehyde crosslinking chamber at 25° C., at 95% relative humidity and excess formaldehyde vapor for 60 minutes. The crosslinked collagen matrix is evacuated to remove residual formaldehyde and the individual vascular wound dressings are packaged for sterilization.

EXAMPLE 3

Preparation of Resorbable Vascular Wound Dressings Incorporated with Heparin.

A collagen dispersion is prepared in accordance with Example 2. Heparin solution (collagen:heparin=50:1 w/w) is slowly added to the dispersion while mixing. The thoroughly mixed collagen/heparin gel is then processed in accordance with Example 2.

EXAMPLE 4

Preparation of Resorbable Vascular Wound Dressings Containing Coiled Filament al Support A polyglyconate filament such as a maxon suture is first wound onto a 0.4 cm O.D. mandrel. The subsequent process is identical to the Example 2.

EXAMPLE 5

Method of Use of a Resorbable Vascular Wound Dressing with a PTA Balloon Catheter During Peripheral Vessel Angioplasty Repair.

A PTA balloon catheter with a vascular wound dressing folded over the balloon is inserted through the femoral artery via a percutaneous puncture site. The balloon with the wound dressing is guided to the selected vessel site via a guide wire. The protective sheath is removed by pulling the attached string. The balloon is inflated until a full resistance is reached at about 5 psi to about 7 psi. The balloon is deflated and the catheter removed, leaving the vascular wound dessing in its expanded form.

EXAMPLE 6

Method of Use of a Resorbable Vascular Wound Dressing With a PTA Catheter for Post Peripheral Vessel Angioplasty Vessel Repair.

A PTA catheter with a self expandable vascular wound dressing, made in accordance with the present invention, folded at the tip of the catheter is inserted through the femoral artery via a percutaneous puncture site. The wound dressing is guided to the selected vessel site via a guide wire. The protection sheath is removed by pulling the attached string. The folded wound dressing self expands to adhere to the vessel wall. The catheter is then removed.

EXAMPLE 7

Method of Use of a Resorbable Vascular Wound Dressing With a PTCA Balloon Catheter During Coronary Angioplasty Vessel Repair.

A percutaneous transluminal coronary angioplasty (PTCA) catheter with a resorbable vascular wound dressing folded over the balloon made in accordance with the present invention is inserted through an artery via a percutaneous puncture site. The balloon with the wound dressing is guided to the selected site within a coronary artery via a guide wire. The protection sheath is removed via a pull of the string. The balloon is inflated until a full resistance is reached at about 5 psi to about 7 psi, corresponding to a fully expanded vascular wound dressing. The balloon is then deflated and catheter removed, leaving the expanded wound dressing at the repair site.

EXAMPLE 8

Method of Use of a Resorbable Vascular Wound Dressing With a PTCA Catheter for Post Angioplasty Coronary Vessel Repair.

A PTCA catheter with a folded vascular wound dressing at the tip of the catheter, made in accordance with the present invention, is guided to the lesion site within a coronary artery. The protection sheath is removed by pulling the string to free the wound dressing. The dressing self expands to adhere to the vessel wall. The catheter is then removed.

EXAMPLE 9

Method of Use of a Resorbable Vascular Wound Dressing At the Anastomotic Sites Within a Vessel.

The vascular wound dressing of the present invention is used at anastomotic sites in conjunction with a vascular surgery procedure. The vascular wound dressings made in accordance with the present invention are inserted from both the proximal and distal ends to the host vessel and the vascular graft. The outside diameter of the vascular wound dressing is chosen to fit the inside diameter of the host vessel and the graft. The vascular wound dressing adheres to the vessel walls of both the host vessel and the graft at the anastomotic sites.

EXAMPLE 10

Method of Use of a Resorbable Vascular Wound Dressing at the Anastomotic Sites Outside the Vessel.

Vascular wound dressings made in accordance with the present invention are inserted from the proximal and distal ends of the anastomotic sites outside the vessel walls. The inside diameter of the vascular wound dressing is chosen to fit the outside diameter of the host vessel and the graft. Upon completion of the anastomotic procedure, the vascular wound dressings are pulled to cover the anastomotic sites.

EXAMPLE 11

Characterization of the Resorbable Vascular Wound Dressings

The properties of vascular wound dressings are characterized below:

a) Density (g/cm$^3$)

The apparent density of the vascular wound dressing made in accordance with the Example 2 is determined by first weighing the wound dressing to obtain the weight. The volume of the wound dressing is then determined from the following formula:

$$V(cm^3) = 3.14 \times [(OD^2/4) - (ID^2/4)] \times h$$

where
OD = outside diameter of the dressing (cm)
ID = inside diameter of the dressing (cm)
h = length of the dressing (cm).

The density (g/cm$^3$) is then calculated from the weight and volume of the vascular wound dressing.

The density of the vascular wound dressings of the present invention is from about 0.05 g/cm$^3$ to about 0.8 g/cm$^3$.

b) Compliance (% radial change per mm Hg$\times 10^{-2}$)

A balloon is inserted into the lumen of a vascular wound dressing made in accordance with the Example 2. The outside diameter of the dressing is measured with a cathetometer. The balloon is inflated and the pressure inside the balloon is recorded. The outside diameter of the pressurized wound dressing is then measured. The average compliance is calculated as percent change in diameter per mm Hg$\times 10^{-2}$.

$$\text{Compliance} = \left[ \frac{OD_f - OD_o}{OD_o \times [P_f - P_o]} \right]$$

Where
$OD_f$ = final outside diameter of the wound dressing (mm)
$OD_o$ = initial outside diameter of the wound dressing (mm)
$P_f$ = final pressure inside the balloon (mm Hg)
$P_o$ = initial pressure inside the balloon (mm Hg)

The compliance of the present invention is from about 2.0% radial change per mm Hg$\times 10^{-2}$ to about 7.0% radial change per mm Hg$\times 10^{-2}$.

c) Pores (um)

The pore structure as seen by scanning electron micrographs of cross-sectional areas of the vascular wound dressing made in accordance with Example 2 are measured. The porous structure of the vascular wound dressings of the present invention is such that long axis of the pores are aligned circumferentially and the short axis of the pores are perpendicular to the circumference. The pore size is calculated as the average between the long axis and the short axis of each pore.

It is determined that the vascular wound dressings of the present invention have pores in the range of from about 0.1 um to about 150 um.

d) Swelling (g/g)

The swelling is measured by the amount of solution uptake per unit weight of the vascular wound dressing made in accordance with the Example 2. The dry weight of the wound dressing is first determined. The wound dressing is next immersed in a buffered solution, pH 7.4 at 25° C. for one hour. The wet weight is then determined. The swelling (g/g) of the wound dressing is calculated as the difference of the wet weight and the dry weight of the wound dressing divided by the dry weight of the wound dressing.

The swelling of the wound dressings of the present invention is from about 0.5 g/g to about 15 g/g.

e) Shrinkage Temperature (° C.)

A segment of the vascular wound dressing is immersed in a buffered solution bath, pH 7.4. The length is recorded with a cathetometer. The temperature of the solution is raised at a rate of 1° C./minute. The temperature and the length of the samples are continuously recorded until sample shrinks and a constant length maintained. The shrinkage temperature is defined as the temperature where 50% change of the sample length occurs. The shrinkage temperature of the wound dressings of the present invention is from about about 55° C. to about 85° C.

f) Wall Thickness (mm)

The wall thickness of the vascular wound dressing is measured with a micrometer. The wall thickness of the wound dressing is in the range of from about 0.1 mm to about 1.5 mm in the center of the dressings and in the range of from about 0.05 mm to about 0.3 mm at the distal ends of the dressings.

g) Relaxation Recovery Time (second)

The vascular wound dressing is first mechanically deformed by folding to a compact configuration similar to that folded at the tip of a catheter. The mechanically deformed wound dressing is then soaked in a phosphate buffered saline solution, pH 7.4 at 25° C. The time which takes for the deformed wound dressing to return to the original configuration is recorded as the relaxation recovery time.

The wound dressings of the present invention have a relaxation recovery time in the range from about 1 second to about 30 seconds.

What is claimed is:

1. A self-expandable vascular wound dressing for treating a blood vessel comprising a conduit having walls comprised of type I collagen matrix material having pores with an average diameter of from about 0.1 μm to about 150 μm, a density of from about 0.05 g/cm$^3$ to about 0.8 g/cm$^3$, and an inwardly converging tapered inner diameter.

2. The wound dressing of claim 1 having a wall thickness of from about 0.05 mm to about 0.30 mm at its ends and from about 0.1 mm to about 1.5 mm at its center.

3. The wound dressing of claim 2 having an inner diameter of from about 2 mm to about 30 mm.

4. The wound dressing of claim 1 having a compliance of from about 2.0% radial change per mm Hg×10$^{-2}$ to about 7.0% radial change per mm Hg×10$^{-2}$.

5. The wound dressing of claim 1 having a swelling capacity of from about 0.5 g/g to about 15 g/g.

6. The wound dressing of claim 1 having a shrinkage temperature of from about 55° C. to about 85° C.

7. The wound dressing of claim 1 having a relaxation recovery time of from about 1 second to about 30 seconds in an aqueous solution.

8. The wound dressing claim 1 further containing medicaments comprising antibiotics, aspirin, coumadin, polyanionic polysaccharides, prostaglandins, plasminogen activators, glycoproteins, wound healing agents, type II through type XII collagens, and mixtures thereof.

9. The wound dressing of claim 1 which is resorbable in vivo in about 30 days to about 120 days.

10. A self-expandable vascular wound dressing for treating a blood vessel comprising a conduit having walls comprised of type I collagen matrix material having pores with an average diameter of from about 0.1 μm to about 150 μm and an inwardly converging tapered inner diameter; said walls having a thickness of from about 0.05 mm to about 0.30 mm at its ends and from about 0.1 mm to about 1.5 mm at its center; said conduit having an inner diameter of from about 2 mm to about 30 mm, a density of from about 0.05 g/cm$^3$ to about 0.8 g/cm$^3$, a compliance of from about 2.0% radial change per mm Hg×10$^{-2}$ to about 7.0% radial change per mm Hg×10$^{-2}$, and a swelling capacity of from about 0.5 g/g to about 15 g/g.

11. The wound dressing of claim 10 having a shrinkage temperature of from about 55° C. to about 85° C.

12. The wound dressing claim 10 having a relaxation recovery time of from about 1 second to about 30 seconds in an aqueous solution.

13. The wound dressing of claim 10 further containing medicaments comprising antibiotics, aspirin, coumadin, polyanionic polysaccharides, prostaglandins, plasminogen activators, glycoproteins, wound healing agents, type II through type XII collagens, and mixtures thereof.

14. The wound dressing of claim 10 which is resorbable in vivo in about 30 days to about 120 days.

* * * * *